United States Patent [19]

Salia-Munoz

[11] Patent Number: 4,577,943
[45] Date of Patent: Mar. 25, 1986

[54] METHOD AND APPARATUS FOR SELF-EXAMINATION OF THE OCULAR GLOBE

[76] Inventor: Miguel Salia-Munoz, 7a. Privada de Azafran Col., Granjas, Mexico

[21] Appl. No.: 459,967

[22] Filed: Jan. 21, 1983

[30] Foreign Application Priority Data

Aug. 27, 1982 [MX] Mexico .................................. 194193

[51] Int. Cl.⁴ ............................ A61B 3/10; A61B 3/00
[52] U.S. Cl. .................................... 351/205; 351/218; 351/221; 351/246; 351/223
[58] Field of Search ............... 351/205, 218, 221, 246, 351/223

[56] References Cited

U.S. PATENT DOCUMENTS 1,662,150  3/1928  Kerr ................................. 351/221 X
1,678,681  7/1928  Poser .................................... 351/218
3,698,099  10/1972  Matsumura ..................... 351/221 X
3,809,072  5/1974  Ersek et al. ........................... 128/23
3,903,870  9/1975  Berndt ................................. 351/223

Primary Examiner—Rodney B. Bovernick
Attorney, Agent, or Firm—Darby & Darby

[57] ABSTRACT

A method of self-examining the interior of the ocular globe by applying a light source to the outer surface of the lower eyelid, with the eye closed in order to permit the entrance of the light from said light source only through the thickness of said lower eyelid and without said light passing through the crystalline or other focusing element of the eye, whereby the inner structure of the eye is rendered visible to the patient. An apparatus for carrying out the method includes a light source housed in a casing having a transparent smooth cover adapted to be contacted under a slight pressure with the exterior surface of the lower eyelid, and a power source for the light source.

3 Claims, 4 Drawing Figures

METHOD AND APPARATUS FOR SELF-EXAMINATION OF THE OCULAR GLOBE

FIELD OF THE INVENTION

The present invention refers to a method of self-examination of the interior of the ocular globe and, more particularly, it is related with an apparatus for interiorly examining the ocular globe, taking advantage of the reflective properties of the interior surfaces thereof.

BACKGROUND OF THE INVENTION

As is well known in the techniques of examining the interior surfaces of the ocular globe, in order to determine certain defects thereof, said examination must be carried out by the use of special apparatus which throw luminous beams which are very straight and thin, and which must be passed through the iris of the eye and through the crystalline, in order to examine certain areas, for instance, of the cornea or the retina, but requiring very intricate installations and, also, with the practical impossibility of examining certain regions of the interior of the ocular globe, which are not accesible through the iris which covers the majority of the cornea in its section giving access to the light rays towards the interior of the ocular globe.

Therefore, the above described system requires that, if a person wishes to detect certain defects in his vision so that he may decide to visit the ophthalmologist in order for him to determine the nature of the problems, a relatively long time elapses, giving as a result that the disease which, at the outset could have been easily remedied, turns out to be occasionally practically incurable or only curable with great difficulties.

Therefore, it has been for long sought to introduce a method and an apparatus permitting the user to self-examine the interior of the ocular globe such that, with certain very elementary training, he may determine himself when any part of the interior of his ocular globe is defective, so as to immediately proceed to visit the ophthalmologist to apply the adequate treatment. The customary reluctancy to visit medical doctors and particularly ophthalmologists, very often renders the defects or diseases of the ocular globe very grave and permits them to advance so as to become practically incurable, so that an apparatus of this nature, together with the method of the present invention, which permits self-examining the interior of the ocular globe, may solve very serious problems as a preventing apparatus and method for avoiding the ocular diseases to develop to an undue stage.

BRIEF SUMMARY OF THE INVENTION

Having in mind the defects of the prior art techniques, it is an object of the present invention to provide a method of self-examination of the ocular globe, which is very simple to carry out and does not require any intricate installations.

It is another object of the present invention to provide an apparatus for self-examining the interior of the ocular globe, which is very simple in construction and yet of high efficiency for the exposure of the interiors of the ocular globe.

It is one other object of the present invention to provide an apparatus for self-examining the ocular globe, of the above mentioned character, which will permit the user to self-examine his eyes without any problem.

One other object of the present invention is to provide an apparatus of the above mentioned character, which will provide sufficient illumination for detecting the images of the interior of the ocular globe and in the retina for transmission to the brain, taking advantage of the reflective properties of the interiors of the ocular globe.

BRIEF DESCRIPTION OF THE DRAWINGS

The novel features that I consider characteristic of my invention are set forth with particularity in the appended claims. The invention itself, however, both as its organization and its method of operation, together with additional objects and advantages thereof, will best be understood from the following description of certain specific embodiments, when read in connection with the accompanying drawings, in which:

Figure 1:
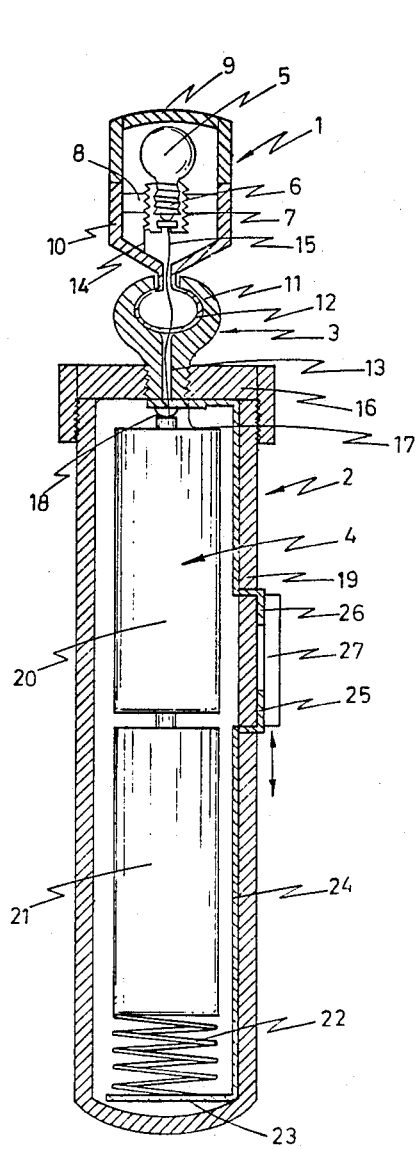
FIG. 1 is a cross-sectional view of an embodiment of the apparatus for self-examining the ocular globe, showing its inner details.

Having now more particular reference to the drawings wherein like parts are designated by like reference numerals, and more specifically to FIG. 1 thereof, there is shown an apparatus for self-examination of the ocular globe, built in accordance with a first embodiment of the present invention, which comprises a light source 1, a handle 2, a movable mounting 3 connected between the light source and the handle, and a power source 4 to supply power to said light source.

More particularly, the light source 1 of the apparatus built in accordance with the first embodiment of the present invention, comprises a bulb or any other similar illuminating device 5, provided with a plug section which, in the example illustrated, comprises a threaded end 6, which is introduced within an also conventionally threaded receptacle 7, supported by means of brackets 8 within the housing 10 of the light source 1. The extreme portion of the housing 10, which is illustrated by means of the reference numeral 9, comprises a transparent material, in order to permit the light beams from the bulb 5, to pass directly through the transparent surface 9, to be applied to the eye of the user as will be explained in more detail hereinbelow.

The housing 10 is provided with a hollow spherical spigot portion 12, introduced within a bell 11 having a hole 13 so that one of the leads from receptacle 7, particularly lead 15, may pass directly through the bell and spigot connection to reach a terminal 18, supported on an insulating plate 17, and to be connected to the power source as will be described hereinbelow. The other lead from receptacle 7 and illustrated under reference numeral 14, is directly connected to ground in the housing 10.

The spigot 12 is introduced in the cover 16 of the handle 2 and said handle 2 constitutes an elongate cylindrical housing within which the power source 4 is introduced, said power source comprising, for instance, two dry batteries 20 and 21, connected in series, which positive pole is connected to terminal 18 and which negative pole is connected, through a conventional spring, to the plate 23 which is at the opposite end of handle 2, so that, through a connector 24, it will be in turn connected to ground with the housing 10 and, therefore, through the conductor 14 to the opposite pole of receptacle 7, such as clearly illustrated in FIG. 1 of the drawings. In order to switch on and off the device at will, a conventional switch is provided in the form of a sliding switch 27, which is operated within a gap provided in the connector 24, by means of terminals 25 and 26 which are connected and disconnected in accordance with the position of the sliding switch 27, such as will be clearly apparent to anyone which may be skilled in the art and such as illustrated in FIG. 1 of the drawings.

With the above, the circuit of the apparatus in accordance with this first embodiment of the present invention and illustrated in FIG. 1 is completed, whereby the light source 1 will be switched on and off at will, in order to carry out the examination of the eye as will be described hereinbelow.

Figure 2:
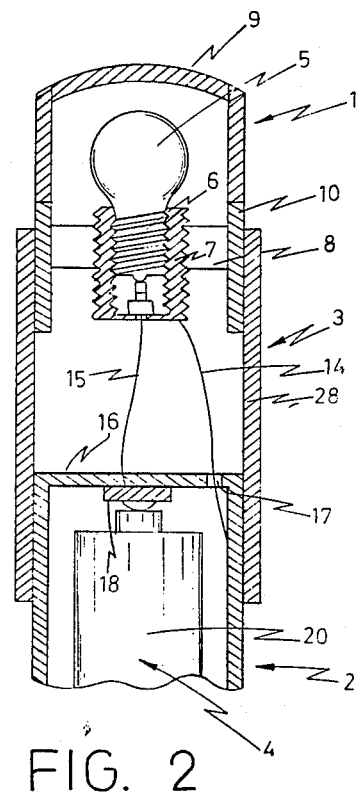
FIG. 2 is a fragmentary cross-sectional view of a second embodiment of the apparatus for self-examination of the ocular globe.

FIG. 2 of the drawings illustrates a simplifed embodiment of the present invention and this second embodiment is similar to that illustrated in FIG. 1, with the only difference that, in lieu of a bell and spigot connection 3, said connection 3 between the light source 1 and the body of the handle 2, is carried out through a plastic tube 28, which is introduced with a pressure fit on the lower end of the housing 10 of the light source 1 and around the upper end of the body 19 of handle 2. Otherwise, the performance of the device built in accordance with this second embodiment, is exactly the same as that of the first embodiment of the invention.

Figures 3, 4:
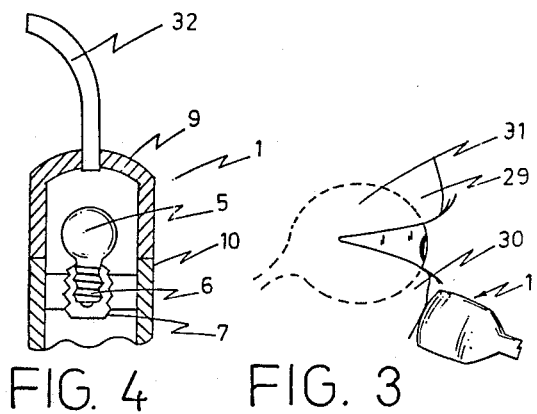
FIG. 3 is a diagram showing the manner of applying the device of the present invention for carrying out the method of self-examination of the ocular globe.
FIG. 4 is a fragmentary cross-sectional view of a third embodiment of the apparatus.

FIG. 4 illustrates a third embodiment, which is of similar construction to the two first embodiments described above, but with its end connected to an optical fiber 32, which permits the use of the apparatus between the glasses that may be worn by the user and the eyelid, said glasses to be preferably optical grid glasses, as those described and claimed in copending U.S. patent application Ser. No. 341,019, filed by the same applicant, inasmuch as it is only necessary to apply the end of the optical fiber against the lower eyelid.

The mode of operation of the apparatus built in accordance with the present invention, in order to carry out the method of self-examination of the interior of the ocular globe, is to apply the curved end surface 9 of the light source 1, or the end of the optical fiber 32, to the lower eyelid 30 of the user, in the position clearly illustrated in FIG. 3 of the drawings, such that, when the eyelid 30 is closed against the eyelid 29, the ocular globe 31 will be darkened and the interiors of said ocular globe 31 will be only and profusely illuminated by the light source 1 of the apparatus of the present invention, so that said indirect illumination, carried through the translucent lower eyelid 30, will illuminate all the interior of the eye, such that, taking advantage of the reflective property of the interiors of said eye, certain parts of the retina may detect, in accordance with the illuminated zone of the ocular globe, all the interior details thereof which, surprisingly, as has been determined, may be observed very neatly, because the perception of said interior parts of the ocular globe is directly through the light sensitive cells of the retina, without passing through a lens or focusing device such as the crystalline of the eye.

The light source 1 may be moved at will by means of the orientation thereof with respect to the body of the handle 2, by using the flexible connection 3 which has been described above, or else by displacing the optical fiber 32 at will, in order to illuminate the various sections of the ocular globe that may be necessary to examine by the same user.

The above permits, such as will be apparent to anyone skilled in the art, the self-examination of the eye and the determination of the diseases that may be suffered thereby, provided that the user is trained at least elementarily, so as to provide sufficient knowledge to him to make him able to self-examine his ocular globe, and may thereafter visit the ophthalmologist with the necessary information so that the latter may determine the disease and proceed to the curative action therefor.

Although I have shown and described certain specific embodiments of my invention, I am fully aware that many modifications thereof are possible. My invention, therefore, is not to be restricted except insofar as is necessitated by the prior art and by the spirit of the appended claims.

What I claim is:

1. A method of self-examining by a patient of the interior of the ocular globe, which comprises applying a light source to the outer surface of the lower eyelid, with the eye closed in order to permit the entrance of the light from said light source only through the thickness of said lower eyelid and without said light passing directly through the crystalline or other focusing element of the eye, whereby the interior structure of the eye is rendered visible to the patient directly through perception by the light sensitive cells of the retina.

2. A method according to claim 1 wherein the application of said light source to the outer surface of the lower eyelid further comprises providing a light bulb of a size sufficiently small to permit said application, surrounding said light bulb with a transparent cover, and contacting said transparent cover with the outer surface of said lower eyelid.

3. A method according to claim 1 wherein the application of said light source to the outer surface of the lower eyelid further comprises providing a light bulb, surrounding said light bulb with an opaque cover, providing an optical fiber through said opaque cover and extending through a distance outwardly thereof to from an extended fiber having an illuminating extreme end, and contacting said extreme end of the optical fiber with the outer surface of said lower eyelid.

* * * * *